United States Patent [19]

Hayashi

[11] 4,330,745
[45] May 18, 1982

[54] METHOD AND APPARATUS FOR COUNTING BLOOD PLATELETS

[75] Inventor: Norihito Hayashi, Hyogo, Japan

[73] Assignee: Toa Medical Electronic Co., Ltd., Hyogo, Japan

[21] Appl. No.: 151,579

[22] Filed: May 20, 1980

[30] Foreign Application Priority Data

May 28, 1979 [JP] Japan .................................. 54/65936

[51] Int. Cl.³ ............................................. G01N 27/00
[52] U.S. Cl. ............................ 324/71 CP; 235/92 PC
[58] Field of Search ............... 324/71 CP; 235/92 PC

[56] References Cited

U.S. PATENT DOCUMENTS

| | | | |
|---|---|---|---|
| 3,963,983 | 6/1976 | Hogg | 324/71 CP |
| 3,970,928 | 7/1976 | Kachel | 324/71 CP |
| 3,973,189 | 8/1976 | Angel | 324/71 CP |
| 4,009,435 | 2/1977 | Hogg | 324/71 CP |
| 4,157,499 | 6/1979 | Kacerek | 324/71 CP |

Primary Examiner—Michael J. Tokar
Attorney, Agent, or Firm—Pearne, Gordon, Sessions, McCoy & Granger

[57] ABSTRACT

Precise counting of blood platelets is achieved by discriminating electrical pulse signals derived from blood platelets suspended in a diluted blood sample from electrical pulsive signals derived from red blood cells also suspended in the sample and correcting the count of platelets on the basis of a correction formula that uses the electrical pulsive signal derived from red blood cells as a correction parameter.

7 Claims, 8 Drawing Figures

METHOD AND APPARATUS FOR COUNTING BLOOD PLATELETS

BACKGROUND OF THE INVENTION

This invention relates to a method and apparatus for counting the blood platelets in blood.

The counting of blood platelets has been conventionally achieved by the plural platelet plasma method (PRP method or Bull's correction) that requires the preliminary treatment of a sample or the visual observation method that needs the preparation of a specimen. According to the PRP method, a blood sample in a capillary tube is let stand or centrifuged to settle red blood cells and white blood cells in layers and recover the layers of platelets and plasma which are passed through a corpuscle counter to count platelets one by one. In this method, the suspension of blood platelets is concentrated to separate red blood cells and white blood cells, the count of platelets is corrected by a corrective value related to a separately determined hematocrit of blood to convert the count to the number of platelets in a unit volume of blood. The PRP method achieves relatively high accuracy without requiring skill in preparing a sample, but on the other hand, preparing layers of platelets and plasma requires a lot of time and effort, the slightest presence of red blood cells can cause a great error, and the process of conversion by correction is cumbersome. For these reasons, it is difficult to perform the PRP method automatically.

The visual observation method depends on direct counting of platelets in a blood preparation observed under a microscope. The disadvantages of this method are non-uniformity of platelet distribution in the preparation, a lot of skill needed to make the preparation, and platelets easily destroyed by being deposited on the glass to which the blood sample is fixed.

Therefore, one object of this invention is to provide a method and apparatus for achieving automatic and accurate counting of blood platelets on the basis of simple dilution of a blood sample as is required in the counting of red blood cells.

Another object of the invention is to provide an automatic platelet counting method that involves ony the RBC count as a parameter for correcting the count of platelets and which outputs the final result through a relatively simple arithmetic operation.

A further object of the invention is to provide an automatic platelet counting apparatus that can be manufactured at relatively low cost because of the relative simplicity of the platelet counting principle on which it operates.

Still another object of the invention is to provide an even simpler and more accurate method and apparatus for blood platelet counting which is particularly adapted for clinical screening as a preliminary examination.

The automatic counting technique of this invention can be incorporated in a conventional automatic blood analyzer that permits simultaneous counting of such parameters as RBC count, WBC count, hemoglobin value and hematocrit. By so doing, the number of blood platelets can be counted simultaneously with the determination of other blood parameters.

When a diluted suspension of whole blood is immediately subjected to the counting of platelets, the suspension is sucked into the detector and corpuscles other than platelets that are suspended near a very small opening for detecting a change in electrical impedance that occurs upon a corpuscle passing through the opening enter that opening by "entrainment" to produce an unwanted pulse signal and cause an error. The conventional technique to prevent the entrance of unwanted corpuscles has been focused on the improvement of the construction of the detecting area, for example, all corpuscles such as red blood cells and platelets are sucked through an opening in a double-walled detector while a clean diluted sample is being supplied from around the opening. This improvement enables blood platelets to be counted with satisfactory accuracy by simply discriminating the peaks of individual electrical pulses generated by corpuscles which pass through the opening, but the improvement has never been implemented in a commercial analyzer because it is difficult and costs high to supply a clean dilution free of any foreign matter and unwanted corpuscle and to fabricate a very small double-walled detection area.

The basic principle of this invention is the same technique that detects the passage of a corpuscle by a change in electrical impedance, except that it corrects the count of platelets by the number of electrical output pulses due to red blood cells (including white blood cells) on the basis of the statistically calculated increase in the number of pulses caused by the entrainment of red blood cells (including white blood cells to pass through the detection area).

DETAILED DESCRIPTION OF THE INVENTION

The statistical technique on which the method of this invention bases could be reached only after many runs of experiment and calculation. We first assumed that the difference between the count of platelets by the pulse peak discrimination method and that obtained by the PRP method or visual observation method (hereunder collectively referred to as the conventional method) is in proportion to the number of red blood cells in a sample (the number of white blood cells which is far smaller than the RBC count is neglible) and calculated to constant K in the formula:

Count by our method − count by the conventional method =

$$K \cdot \frac{RBC}{100}$$

(wherein RBC is the number of red blood cells as expressed in $10^4/mm^3$). Using the obtained average value K (=4.66) as a correction parameter, we calculated the corrected count of platelets. The coefficient ($\gamma$) of the correlation between the uncorrected count by our method and the count by the conventional method was 0.9072, and after the correction by the average value of K. the coefficient reduced to 0.8474. This indicates that when the number of platelets is counted by the pulse peak discrimination method using the correction formula:

Corrected count by our method=(uncorrected) count by our method−a0 (wherein a0 is a constant), the coefficient of the correlation between our method and the conventional method is $\gamma = 0.9072$. It also seems to suggest that the correlation does not depend on the RBC count.

As described above, the predominant factor of an error in the platelet count is an additional RBC count due to entrainment, and so, it was necessary to incorporate that factor in a significant correction formula. We therefore checked the reproducibility of the platelet count by repeating our method on the same sample and found that it was very poor due to the entrance of red blood cells within the detector.

Following this finding, we tried a correction by polynominal approximation that was based on the method of least squares and which incorporated the formula: Corrected count by our method=(uncorrected) count by our method−a0. The polynominal approximation formula is represented as follows:

Platelet count by our method−count by the conventional method=

$$a0 + a1 \cdot \frac{RBC}{100} + a2 \cdot \left(\frac{RBC}{100}\right)^2 + \ldots + am\left(\frac{RBC}{100}\right)^m$$

Based on this formula, three countings were conducted for each of 48 samples, and the result was checked for its correlation with the conventional method for no correction, m=0, m=1, m=2 m=3. The coefficient of correlation was only about 0.8 for each case. For the first counting, the coefficient was 0.8657 in the absence of correction, and this was little different from 0.8698 which was the coefficient obtained by substituting m=0 and m−1 into the formula. In contrast, for the third counting, the coefficient was 0.9250 in the absence of correction and this increased to 0.9772 by substituting m=0 and m=1 into the formula. We therefore concluded that a satisfactorily high coefficient of correlation was obtained by correcting the third count of platelets for the same sample using the polynominal approximation based on the method of least squares wherein m is 1.

Figure 1:
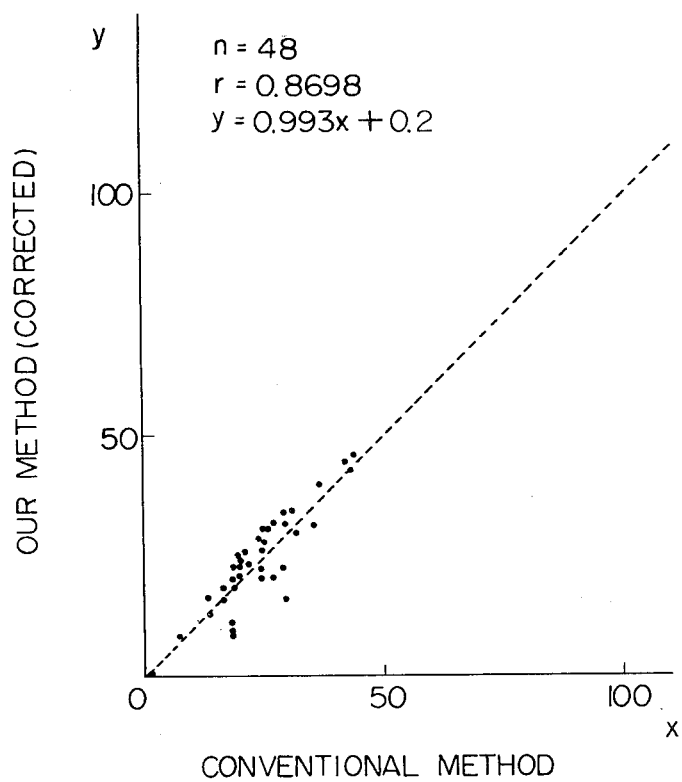
FIGS. 1, 2 and 3 are graphs comparing the platelet counting by our method and that by the conventional method, and each graph shows how much the counting accuracy is improved by taking into account the effect of the RBC counts of the current sample, the last sample, and the last but one sample.
Figure 2:
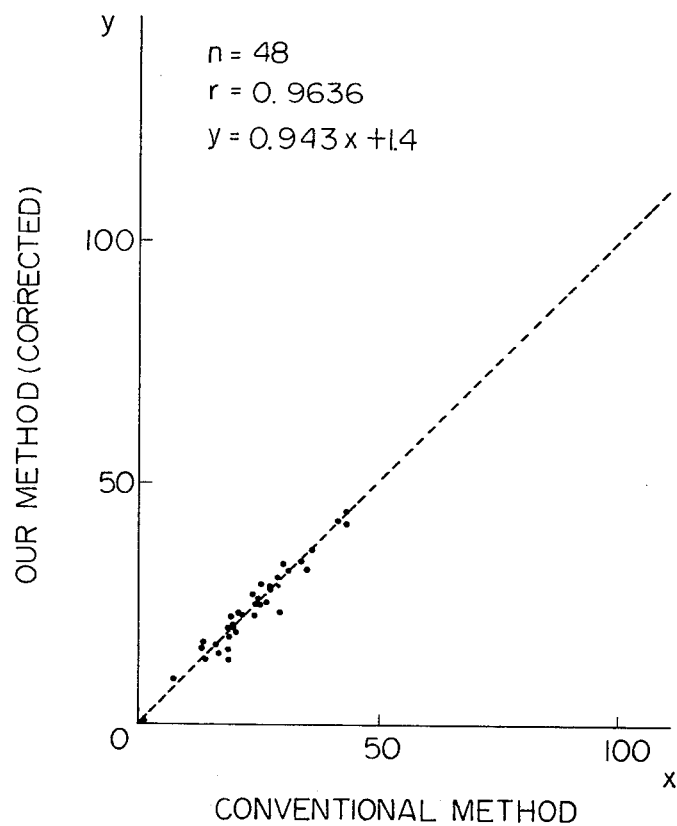

The above mentioned findings are set forth in accompanying FIGS. 1, 2 and 3 and Table 1 below.

TABLE 1

| Sample | Counting conditions and coefficient of correlation | | |
|---|---|---|---|
| | N = 48 | | |
| Counting | 1st | 2nd | 3rd |
| Counting Time | 11.0 sec | 11.0 sec | 11.0 sec |
| Correction | | | |
| NO | 0.8657 | 0.9428 | 0.9250 |
| m = 0 | 0.8657 | 0.9428 | 0.9250 |

TABLE 1-continued

| Sample | Counting conditions and coefficient of correlation | | |
|---|---|---|---|
| | N = 48 | | |
| Counting | 1st | 2nd | 3rd |
| Counting Time | 11.0 sec | 11.0 sec | 11.0 sec |
| m = 1 | 0.8698** | 0.9636 | 0.9772* |

*a0 = 4.79, a1 = 3.31
**a0 = 18.9, a1 = −0.557

Figure 4:
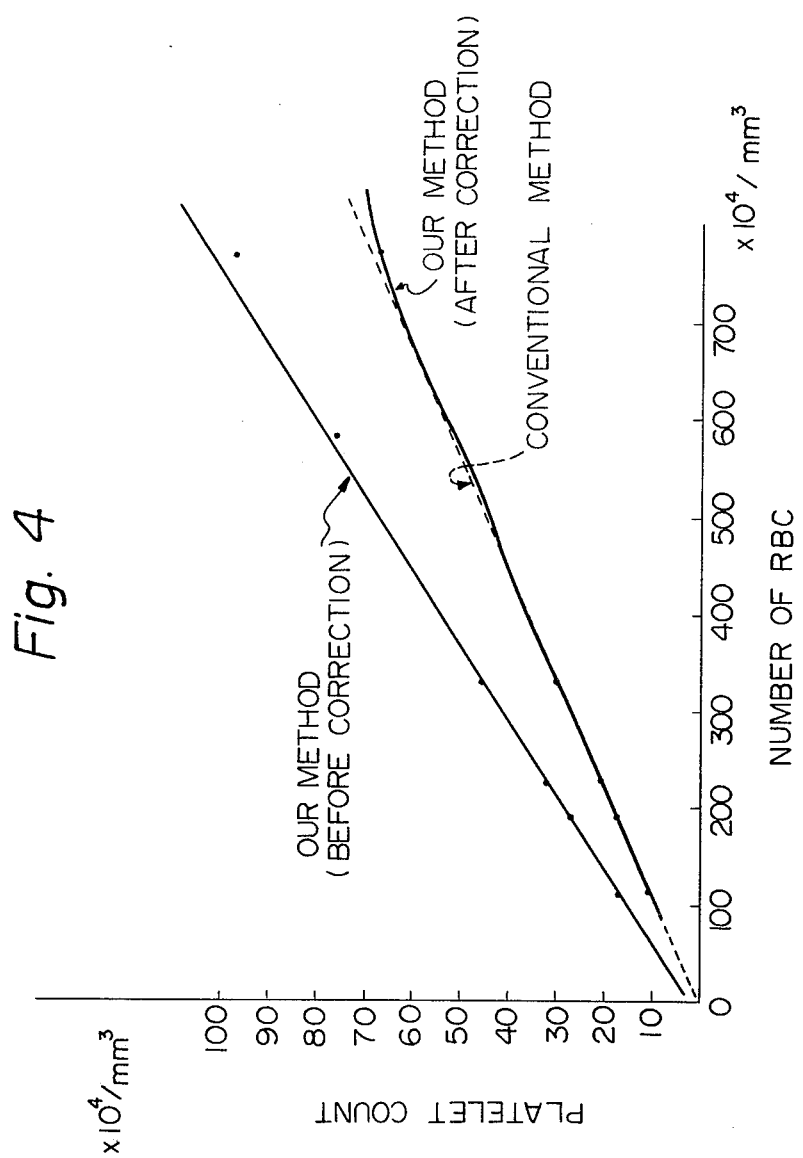
FIG. 4 is a graph showing the correlation between the platelet count and RBC count as measured by the conventional method and our method before and after correction.

In the next place, we checked if the linearity between RBC count and platelet count obtained by our method agreed with the linearity of the same parameters obtained for the same sample by the conventional method. FIG. 4 is a visual representation of the results of the checking, which gives the relation: count by our method=

$$b0 + b1 \cdot \frac{RBC}{100},$$

and this is in perfect correspondence to the above defined formula: Count by our method−count by the conventional method=

$$a0 + a1 \frac{RBC}{100}.$$

Figure 3:
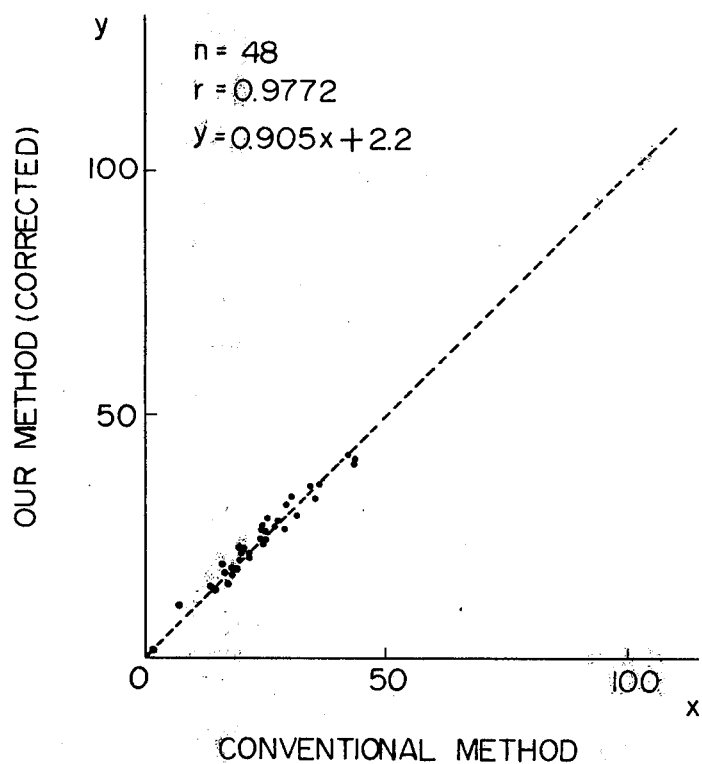

As is clear from Table 1 and FIG. 3, the reproducibility of our method is improved by conducting platelet counting at least three times. We conducted a test with the detector filled with a sample and found that our method exhibited constant platelet counts in repeated counting for samples of various concentrations.

Based on the data set forth above, we learned for sure that the intended object of this invention can be achieved by preparing a suspension of blood corpuscles from a diluted blood (which may be whole blood) sample, detecting discrete electrical pulse signals generated by corpuscles suspended in the sample, counting the first pulses having a peak less than a predetermined pulse peak separately from the second pulses having a peak greater than the predetermined pulse peak, and calculating the number of platelets (PL) (in $10^4/mm^3$) by substituting the count of the first pulses (Pm) (in $10^4/mm^3$) into the following formula:

$$PL + Pm - \left\{a0 + a1 \cdot \frac{RBC}{100} + a2\left(\frac{RBC}{100}\right)^2 + \ldots + am\left(\frac{RBC}{100}\right)^m\right\}$$

Consecutive analysis of different samples can also be made on the basis of the following formula using RBC as a correction parameter:

$$Pm - PL = a0 + a1 \cdot \frac{RBC(i)}{100} + a2 \cdot \frac{RBC(i-1)}{100} + \ldots + am \cdot \frac{RBC(i-(m-1))}{100}$$

wherein RBC(i) is the count of RBCs in the current sample, RBC(i−1) is the count of RBCs in the last sample, and RBC(i−(m−1)) is the count of RBCs in the last but (m−2) sample.

As pointed out before, the current sample, the last sample, the last but one sample, and the last but two sample have an effect on the reproducibility of the platelet count, and in consideration of this fact, we substituted these four samples into the above formula and determined statistically the coefficients a1, a2, a3 and a4 for RBC(i), RBC(i−1), RBC(i−2) and RBC(i−3) as well as the constants a0 on the basis of many runs of experiment. The results were as follows: a0=0.9, a1=0.632, a2=2.56, a3=0.579 and a4=0.683. This gives a formula:

$$PL = Pm - \left(0.9 - 0.632 \cdot \frac{RBC(i)}{100} + 2.56 \cdot \frac{RBC(i-1)}{100} + 0.579 \cdot \frac{RBC(i-2)}{100} + 0.683 \cdot \frac{RBC(i-3)}{100}\right)$$

and the same results as set forth in FIG. 3 were obtained. Once a0, a1, a2, a3 and a4 are set to fixed values, the formula could be applied to different counters of the same model without causing any substantial difference in the result of counting. The counting conditions employed were: the detector had an opening 80 μm in size, had an inside diameter of 6 mm, sucked 0.3 ml of a sample for each counting (0.25 ml of that volume was subjected to actual counting), and finished the counting for each sample in about eleven seconds. Therefore, unless these conditions are changed, the above values of the four coefficients and one constant can be used in platelet counting with different counters of the same model. If some of these conditions are changed, the constant and coefficients a0 to am are better to be determined by calculating Pm−PL for at least thirty samples. The coefficient of correlation obtained for the above formula was $\gamma = 0.9445$.

From the data set forth above, we also found that satisfactorily accurate results could be obtained by using the formula:

$$PL = Pm - 0.0331 \times RBC - 4.8$$

on the basis of three countings. Since the normal RBC count is in the range of from about 450 to 510 ($\times 10^4/mm^3$) for a human male and from about 395 to 465 ($\times 10^4/mm^3$) for a female, the above formula gives a corrective value of from 19.7 to 21.68 for a male, and from 17.87 to 20.19 for a female, with the respective averages being 20.69 and 19.03. The average RBC count without considering the sex difference was from 395 to 510 ($\times 10^4/mm^3$), giving a corrective value of 19.86.

Therefore, if the procedure of analysis permits discrimination between two sexes, an adequately accurate platelet count can be obtained by checking to see if the RBC count is within the normal range (if not, any sign for abnormality is displayed) and by subtracting the corrective values, 20.69 (for male) and 19.03 (for female), from the obtained platelet counts. This simplified formula will prove very efficient when applied to clinical screening. If there is no need of sex discrimination, simply subtracting 19.86 gives a substantially correct platelet count (in $10^4/mm^3$). If the platelet count obtained is found abnormal, the sample should be subjected to counting by the conventional method or a more exacting method or another counting.

As will be understood from the foregoing, this invention provides a simple and quick counting of platelets from the formula: $PL = Pm - C$ by just determining a0 and a1 for thirty or so samples.

Figure 5:
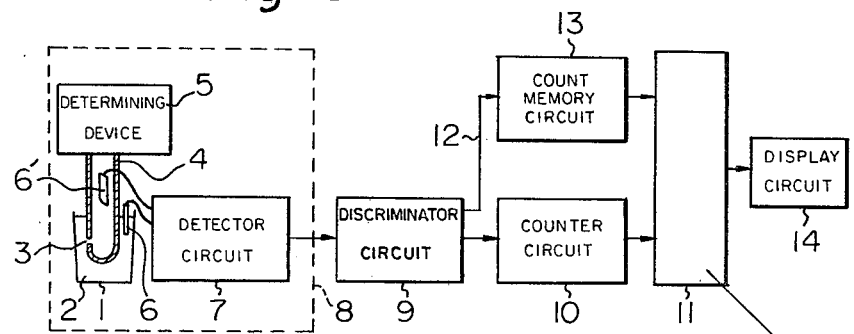
FIG. 5 shows one embodiment of the apparatus for implementing our method.

One embodiment of the apparatus for implementing the method of this invention is described hereunder by reference to FIG. 5. The apparatus schematically shown in the figure is for consecutive analysis of different samples and it determines the platelet count for the current sample through correction based on the RBC counts for the last sample and the last but one sample. A diluted whole blood sample or a suspension of blood corpuscles 2 held in a container 1 is sucked into a detector 4 through a small opening 3 positioned below the level of the suspension, and the quantity of the sucked suspension is determined by a determining device 5. Blood corpuscles that pass through the opening 3 upon suction cause a change in the electrical impedance in the area near the opening, which is detected by electrodes 6, 6' and converted to an electrical pulse signal in a detector circuit 7. The devices 1 to 7 combine together to form a detector apparatus 8.

The detector apparatus 8 generates a pulse output signal which is supplied to a discriminator circuit 9 where an output signal greater than a predetermined pulse peak or threshold level which is considered to derive from red blood cells and white blood cells is descriminated from a pulse output less than the threshold level which is considered to derive from platelets. The discriminated signal output is then supplied to counter circuits 13 and 10; the counter circuit 10 counts all output signals that have passed through the discriminator circuit 9 and derive from red blood cells and platelets. This counting is usually accomplished by, for example, detecting the rising of a pulse with, say, AND comparator. The pulse that has reached the level for RBC in the discriminator circuit 9 is supplied to a count memory circuit 13 through a line 12. The count memory circuit consists of, say, three memory sections for storing the RBC count for the current sample, that for the last sample and that for the last but one sample. Upon each counting operation, the memory of the RBC count for the last but one sample is erased for storing a new RBC count data. It is to be noted that since the WBC count is generally less than a few percent of the RBC count, it may or may not be included in the RBC count, and it has no effect on the counting accuracy so long as its proportion to the RBC count is clearly defined.

The count obtained in the counter circuit 10 includes pulses generated by the entrainment of red blood cells into the detector 4, and so, it is supplied to a corrective arithmetic circuit 11 which performs a corrective arithmetic operation using the correction formula defined above and on the basis of, for example, the RBC counts for the current sample, the last sample, and the last but one sample. The correcting value calculated is subtracted from the count obtained in the circuit 10, and the result is supplied to a display circuit 14 where the corrected platelet count is displayed or printed.

Figure 6:
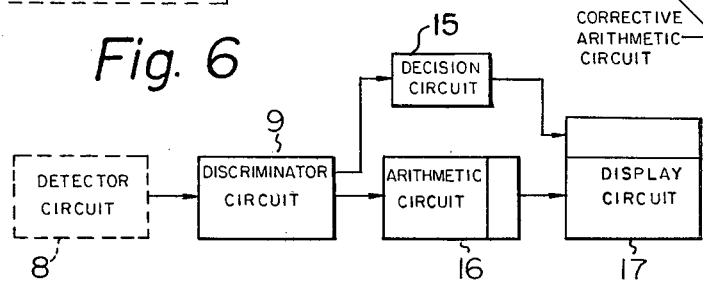
FIG. 6 is a modified type of the apparatus for implementing our method.

FIG. 6 illustrates a simplified version of apparatus which counts platelets by simple subtraction of a predetermined correcting value when the RBC count is found to be in the normal range. The output of the detector 8 is supplied to the discriminator circuit 9 which delivers a pulse output signal that has reached a predetermined threshold level separately from a signal that has not reached such predetermined threshold level. The former pulse signal is considered as the RBC count (which may include the WBC count) and is sent to a count decision circuit 15 which determines whether the RBC count sent is normal or not, and the latter pulse signal is considered as derived from platelets and supplied to a count arithmetic circuit 16 where the aforementioned correcting value (C) is subtracted from the platelet count. The outputs from the decision circuit 15 and the arithmetic circuit 16 are displayed or printed by a display circuit 17. To be more specific, the result indicating whether the RBC count (which may include the WBC count) is within the normal range or not (the result may contain the actual count value) and the corrected count of platelets is displayed by the display circuit 17.

Figure 7:
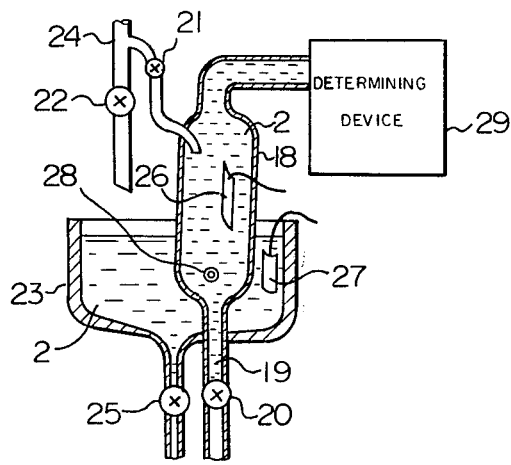
FIGS. 7 and 8 are each a fragmentary sectional view that schematically shows the improvement of external devices for the apparatus of this invention.
Figure 8:
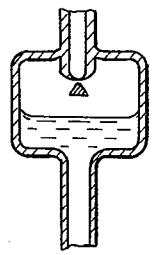

FIGS. 7 and 8 show improvements made in external devices for the detector 4. In FIG. 7, both inside and outside of a detector 18 are filled with the same suspension of blood sample to assure that the RBC count as a correction parameter is kept derived from the RBCs in the current sample. This eliminates the effect of the RBC count derived from the previous samples and permits easy arithmetic operation for correction. The bottom of the detector 18 is connected to a drain pipe 19 which discharges the sample from the detector through a cock 20. A sample suspension 2 is supplied to both the detector 18 and a sample chamber 23 simultaneously through an inlet pipe 24 by opening cocks 21 and 22. Electrodes 26 and 27 can be connected electrically with each other by a small opening 28 made in the wall of the detector 18. When a determining device 29 sucks a predetermined amount of the suspension sample from the sample chamber 23 into the detector 18, blood corpuscles pass through the detection area around the opening 28, causing a change in the electrical impedance across the electrodes 26 and 27. The change is detected by the detector circuit 7 to produce a pulsive output. During the operation of the counter system described above, the determining device, cocks 20, 21 and 22 may be connected electrically with the inside of the detector 18 by the suspension 2 diluted with physiological saline solution, but they must not be connected electrically with other external devices to cause electrical leak. One effective means to prevent this is provide intermittent supply of suspension droplets by a device as shown in FIG. 8.

What is claimed is:

1. A method for counting the number of platelets in blood which comprises:
    preparing a suspension of blood corpuscles from a diluted blood sample;
    detecting discrete electrical pulse signals generated by corpuscles suspended in the sample;
    counting the first pulses having a peak less than a predetermined level separately from the second pulses having a peak greater than the predetermined level; and
    calculating the number of platelets in the suspension by correcting the count of the first pulses on the basis of the formula:

$$PL \ (\times 10^4/\text{mm}^3) = Pm \ (\times 10^4/\text{mm}^3) - \left\{ a0 + a1 \cdot \frac{RBC}{100} + a2 \left( \frac{RBC}{100} \right)^2 + \ldots + am \left( \frac{RBC}{100} \right)^m \right\}$$

wherein PL is the number of platelets; Pm is the first pulse count; a0, a1, a2 ..., am are correction coefficients; RBC/100 is the concentration of red blood cells ($\times 10^4/\text{mm}^3$) in the blood sample.

2. A method for counting the number of platelets in blood which comprises:
    preparing a suspension of blood corpuscles from a diluted blood sample;
    detecting discrete electrical pulse signals generated by corpuscles suspended in the sample;
    counting the first pulses having a peak less than a predetermined threshold level separately from the second pulses having a peak greater than the predetermined threshold level; and
    calculating the number of platelets in the suspension by correcting the count of the first pulses on the basis of the formula:

$$PL \ (\times 10^4/\text{mm}^3) = Pm \ (\times 10^4/\text{mm}^3) - \left( a0 + a1 \cdot \frac{RBC(i)}{100} + a2 \cdot \frac{RBC(i-1)}{100} + \ldots + am \cdot \frac{RBC(i-(m-1))}{100} \right)$$

wherein PL is the number of platelets; Pm is the first pulse count; a0 is a constant; a1, a2, ..., am are correction coefficients for the current sample, the last sample, the last but one sample, ..., the last but (m−2) sample; RBC(i)/100, RBC(i−1)/100, ..., RBC(i−(m−1))/100 are the concentrations of red blood cells ($\times 10^4/\text{mm}^3$) in the current sample, the last sample, the last but one sample, ..., the last but (m−2) sample.

3. A method for counting the number of platelets in blood which comprises:
    preparing a suspension of blood corpuscles from a diluted blood sample;
    detecting discrete electrical pulse signals generated by corpuscles suspended in the sample;
    counting the first pulses having a peak less than a predetermined threshold level separately from the second pulses having a peak greater than the predetermined threshold level; and
    calculating the number of platelets in the suspension by correcting the count of the first pulses on the basis of the formula:

$$PL(\times 10^4/\text{mm}^3) = Pm(\times 10^4/\text{mm}^3) - C$$

wherein PL is the number of platelets; Pm is the first pulse count; and C is a correction constant based on the concentration of red blood cells in the suspension and is 20.69 for a human male, 19.03 for a human female, and 19.86 as an average for both sexes.

4. An apparatus for automatically counting the number of platelets in blood comprising detector means for detecting the corpuscles suspended in a diluted blood sample as discrete pulse signals on the basis of a change in electrical impedance that occurs when corpuscles pass through a small opening in a detector; a discriminator circuit for separating said discrete pulse signals into those representing corpuscles and having a peak less than a predetermined threshold level and those representing red blood cells and white blood cells and having a peak greater than said threshold level; a counter circuit for counting the pulse output signals representing the corpuscles; a count memory circuit for counting and storing the pulse output signals representing the red blood cells and white blood cells; a corrective arithmetic circuit for correcting the output from said counter circuit on the basis of the output from said count memory circuit; and a display circuit for displaying or printing the output from said corrective arithmetic circuit, said count memory circuit storing a plurality of pulse output signals for a corresponding plurality of samples, said corrective arithmetic circuit including means for correcting the output from said counter circuit on the basis of the relationship:

$$PL\ (\times 10^4/mm^3) = Pm\ (\times 10^4/mm^3) - a0 + a1 \cdot \frac{RBC(i)}{100} + a2 \cdot \frac{RBC(i-1)}{100} + \ldots + am \cdot \frac{RBC(i-(m-1))}{100}$$

wherein PL is the number of platelets; Pm is the first pulse count; a0 is a constant; a1, a2, ..., am are correction coefficients for the current sample, the last sample, the last but one sample, ..., the last but (m−2) sample; RBC(i)/100, RBC(i−1)/100, ..., RBC(i−(m−1))/100 are the concentrations of red blood cells ($\times 10^4/mm^3$) in the current sample, the last sample, the last but one sample, ..., the last but (m−2) sample.

5. An apparatus for automatically counting the number of platelets in blood comprising detector means for detecting the corpuscles suspended in a diluted blood sample as discrete pulse signals on the basis of a change in electrical impedance that occurs when corpuscles pass through a small opening in a detector; a discriminator circuit for separating said discrete pulse signals into those representing the corpuscles and having a peak less than a predetermined threshold level and those representing red blood cells and white blood cells and having a peak greater than said threshold level; a count decision circuit for determining whether the count of pulse output signals representing red blood cells and white blood cells and having a peak greater than said threshold level is within the normal range; a count arithmetic circuit for both counting the pulse output signals representing corpuscles and performing simple subtraction of a predetermined correcting value, and a display circuit for displaying or printing, based on the individual outputs from said count arithmetic circuit, the result indicating whether the counts of red blood cells and white blood cells are within the normal range and the corrected count of platelets, said count arithmetic circuit including means for subtracting said predetermined correcting value on the basis of the relationship:

$$PL(\times 10^4/mm^3) = Pm(\times 10^4/mm^3) - C$$

wherein PL is the number of platelets; Pm is the first pulse count; and C is a correction constant based on the concentration of red blood cells in the suspension and is 20.69 for a human male, 19.03 for a human female, and 19.86 as an average for both sexes.

6. An automatic platelet counting apparatus according to claim 4 wherein both inside and outside of said detector means that communicate each other by said small opening are supplied with substantially the same suspension simultaneously.

7. An automatic platelet counting apparatus according to claim 5 wherein both inside and outside of said detector means that communicate each other by said small opening are supplied with substantially the same suspension simultaneously.

* * * * *

UNITED STATES PATENT AND TRADEMARK OFFICE
CERTIFICATE OF CORRECTION

PATENT NO. : 4,330,745
DATED : May 18, 1982
INVENTOR(S) : Norihito Hayashi

It is certified that error appears in the above—identified patent and that said Letters Patent is hereby corrected as shown below:

Column 2, line 43, "to" should be changed to --the--;

Column 2, line 57, the "." after K should be changed to --,--;

Column 4, line 49, in the formula "PL + Pm" should be changed to --PL = Pm--; and Column 5, line 14, in the formula "$\frac{RBC(-1)}{100}$" should be changed to --$\frac{RBC(i-1)}{100}$--.

Signed and Sealed this

Thirty-first Day of August 1982

[SEAL]

Attest:

GERALD J. MOSSINGHOFF

Attesting Officer

Commissioner of Patents and Trademarks